US010398794B2

(12) United States Patent
Daiku et al.

(10) Patent No.: US 10,398,794 B2
(45) Date of Patent: Sep. 3, 2019

(54) INTERNAL SURFACE ELECTRON BEAM-IRRADIATING DEVICE

(71) Applicant: HITACHI ZOSEN CORPORATION, Osaka (JP)

(72) Inventors: Hiroyuki Daiku, Osaka (JP); Takeshi Noda, Osaka (JP); Ichiro Sakai, Osaka (JP)

(73) Assignee: HITACHI ZOSEN CORPORATION, Osaka (JP)

( * ) Notice: Subject to any disclaimer, the term of this patent is extended or adjusted under 35 U.S.C. 154(b) by 0 days.

(21) Appl. No.: 16/066,578

(22) PCT Filed: Nov. 15, 2016

(86) PCT No.: PCT/JP2016/083800
§ 371 (c)(1),
(2) Date: Jun. 27, 2018

(87) PCT Pub. No.: WO2017/115572
PCT Pub. Date: Jul. 6, 2017

(65) Prior Publication Data
US 2019/0015535 A1    Jan. 17, 2019

(30) Foreign Application Priority Data

Dec. 28, 2015    (JP) .................................. 2015-255594

(51) Int. Cl.
*A61L 2/08*    (2006.01)
*B65B 55/08*    (2006.01)
(Continued)

(52) U.S. Cl.
CPC ................ *A61L 2/087* (2013.01); *A61L 2/26* (2013.01); *B65B 55/08* (2013.01); *G21K 5/04* (2013.01);
(Continued)

(58) Field of Classification Search
USPC ...................................................... 250/396 R
See application file for complete search history.

(56) References Cited

U.S. PATENT DOCUMENTS

| | | | | |
|---|---|---|---|---|
| 6,407,492 B1 * | 6/2002 | Avnery | ................... | H01J 3/027 250/492.3 |
| 8,586,944 B2 * | 11/2013 | Avnery | ................... | B65B 55/08 250/453.11 |

(Continued)

FOREIGN PATENT DOCUMENTS

| | | |
|---|---|---|
| EP | 2650252 A1 | 10/2013 |
| JP | 2002-308231 A | 10/2002 |

(Continued)

OTHER PUBLICATIONS

International Search Report PCT/JP2016/083800 dated Feb. 21, 2017 with English translation.

(Continued)

*Primary Examiner* — Phillip A Johnston
(74) *Attorney, Agent, or Firm* — Pillsbury Winthrop Shaw Pittman, LLP

(57) ABSTRACT

An internal surface electron beam-irradiating device sterilizes the internal surface of a vial by irradiation with an electron beam. The internal surface electron beam-irradiating device includes an electron beam generator that generates the electron beam, a vacuum chamber containing the electron beam generator, an output window that emits the electron beam to the outside of the vacuum chamber, and an extension nozzle that guides an electron cloud formed by extending the electron beam emitted from the output window. The extension nozzle includes a leaking section that leaks the electron cloud. The leaking section includes empty portions that discharge part of the electron cloud to the (Continued)

outside, and a component portion that guides the electron cloud into the leaking section.

4 Claims, 10 Drawing Sheets

(51) Int. Cl.
    *G21K 5/04*     (2006.01)
    *A61L 2/26*     (2006.01)

(52) U.S. Cl.
    CPC ........ *A61L 2202/11* (2013.01); *A61L 2202/23* (2013.01)

(56) References Cited

U.S. PATENT DOCUMENTS

| | | | |
|---|---|---|---|
| 9,850,014 B2 * | 12/2017 | Dickner | ............... A61L 2/087 |
| 9,969,513 B2 * | 5/2018 | Dickner | ............... B67C 7/0073 |
| 2013/0149193 A1 | 6/2013 | Knott et al. | |
| 2016/0009433 A1 | 1/2016 | Tanaka et al. | |
| 2016/0064111 A1 | 3/2016 | Sakai et al. | |

FOREIGN PATENT DOCUMENTS

| | | |
|---|---|---|
| JP | 2008-145291 A | 6/2008 |
| JP | 2009-539718 A | 11/2009 |
| JP | 2013-151327 A | 8/2013 |
| JP | 2014-181039 A | 9/2014 |
| WO | 2007/145561 A1 | 12/2007 |
| WO | 2014/175065 A1 | 4/2014 |
| WO | 2015/113834 A1 | 8/2015 |

OTHER PUBLICATIONS

Extended European Search Report issued in corresponding EP Application No. 16881552.0 dated Dec. 5, 2018.
Notice of Reasons for Refusal dated May 30, 2019 issued in corresponding Japanese Patent Application No. 2015-255594 with English translation.

* cited by examiner

INTERNAL SURFACE ELECTRON BEAM-IRRADIATING DEVICE

CROSS-REFERENCE TO RELATED APPLICATIONS

This is the U.S. National Stage of PCT/JP2016/083800, filed Nov. 15, 2016, which in turn claims priority to Japanese Patent Application No. 2015-255594, filed Dec. 28, 2015, the contents of each of these applications being incorporated herein by reference in their entireties.

TECHNICAL FIELD

The present invention relates to an internal surface electron beam-irradiating device that sterilizes the internal surface of a sterilization object, e.g., a container by irradiation with an electron beam.

BACKGROUND ART

If a company that deals with containers for medical care or foods and drinks faces a medical accident or food poisoning due to insufficient sterilization of containers, the company seriously loses credibility in society. Thus, the internal surfaces of the containers particularly need to be securely sterilized in advanced countries where importance is attached to safety.

At present, as a device for securely sterilizing the internal surface of a container, an internal surface electron beam-irradiating device that can irradiate the internal surface of a container with an electron beam is used. A publicly known internal surface electron beam-irradiating device includes, as shown in FIG. 12, a vacuum nozzle 102 that can be inserted from the opening of a container V so as to emit an electron beam E from an output window 4 (For example, see FIG. 1 of Patent Literature 1). The interior of the vacuum nozzle 102 communicates with an interior of a vacuum chamber (not shown) that is evacuated, thereby forming the electron beam E of accelerated multiple electrons. The electron beam E emitted from the output window 4 provided at tip of the vacuum nozzle 102 is released into the air and collides with air molecules or the like, so that the electron beam F expands as an electron cloud C. The electron cloud C is brought into contact with the internal surface of the container V (a preform in Patent Literature 1), in other words, the electron beam E is emitted to the internal surface of the container V so as to sterilize the internal surface of the container V.

As shown in FIG. 13 (FIG. 2 in Patent Literature 1), Patent Literature 1 also discloses an extension nozzle 105 that is additionally attached, in order to improve the directivity of the electron cloud C, to the tip of the vacuum nozzle 102 shown in FIG. 12.

CITATION LIST

Patent Literature

Patent Literature 1: Japanese Patent Laid-Open No. 2013-151327

SUMMARY OF INVENTION

Technical Problem

In the sterilization of the internal surface of the container V by the internal surface electron beam-irradiating device of Patent Literature 1, a mouth m of the container V is excessively irradiated with the electron beam E as shown in FIG. 12 because of the shape of the electron cloud C. In FIG. 13, a bottom b of the container V is excessively irradiated with the electron beam E, whereas a shoulder s of the container V is insufficiently irradiated with the electron beam E. In this way, if the internal surface of the container V is unevenly irradiated with the electron beam E, the sterilization may become insufficient with low efficiency. This problem becomes serious particularly if a sterilization object is a so-called "square-shouldered" container, e.g., a vial or an eye dropper that has square shoulders and is just barely large enough to let the vacuum nozzle 102 pass through the opening of the container.

An object of the present invention is to provide an internal surface electron beam-irradiating device that can more uniformly irradiate the internal surface of a sterilization object with an electron beam so as to ensure sufficient sterilization with higher efficiency.

Solution to Problem

In order to solve the problem, an internal surface electron beam-irradiating device according to a first invention is an internal surface electron beam-irradiating device for sterilizing the internal surface of a sterilization object having an opening by irradiation of an electron beam, the device including: an electron beam generator configured to generate the electron beam, a vacuum chamber containing the electron beam generator, an output window configured to emit the electron beam to the outside of the vacuum chamber, and an extension nozzle configured to guide an electron cloud formed by extending the electron beam emitted from the output window, the extension nozzle including a leaking section configured to leak the electron cloud, the leaking section including empty portions configured to discharge part of the electron cloud to the outside, and a component portion configured to guide the electron cloud into the leaking section.

An internal surface electron beam-irradiating device according to a second invention is configured such that the leaking section in the internal surface electron beam-irradiating device according to the first invention includes the empty portions at each width in a circumferential direction over a range from an end of the leaking section near the output window to the opposite end of the leaking section.

Moreover, an internal surface electron beam-irradiating device according to a third invention is configured such that in the internal surface electron beam-irradiating device according to the first or second invention, the area ratio of the empty portions and the component portion in the circumferential direction of the leaking section is different from an area ratio in a direction orthogonal to the circumferential direction.

Additionally, in an internal surface electron beam-irradiating device of a fourth invention, the leaking section in the internal surface electron beam-irradiating device according to any one of the first to third inventions is configured such that the total area of the empty portions is larger than the total area of the component portion.

Advantageous Effect of Invention

The internal surface electron beam-irradiating device can more uniformly irradiate the internal surface of a sterilization object with an electron beam, thereby ensuring sufficient sterilization with higher efficiency.

DESCRIPTION OF EMBODIMENTS

An internal surface electron beam-irradiating device according to an embodiment of the present invention will be described below in accordance with the accompanying drawings.

The internal surface electron beam-irradiating device sterilizes the internal surface of a sterilization object having an opening, by irradiation with an electron beam E. The sterilization object having the opening is a so-called "square-shouldered" container, e.g., a vial or an eye dropper that is entirely small in size with square shoulders. As a matter of course, the sterilization object having the opening is not limited to such a container. Any objects including a plastic bottle and a preform are usable as long as the objects are to be sterilized with openings. In the following explanation, for simplicity, the sterilization object having the opening will be discussed as a vial.

Figure 1:
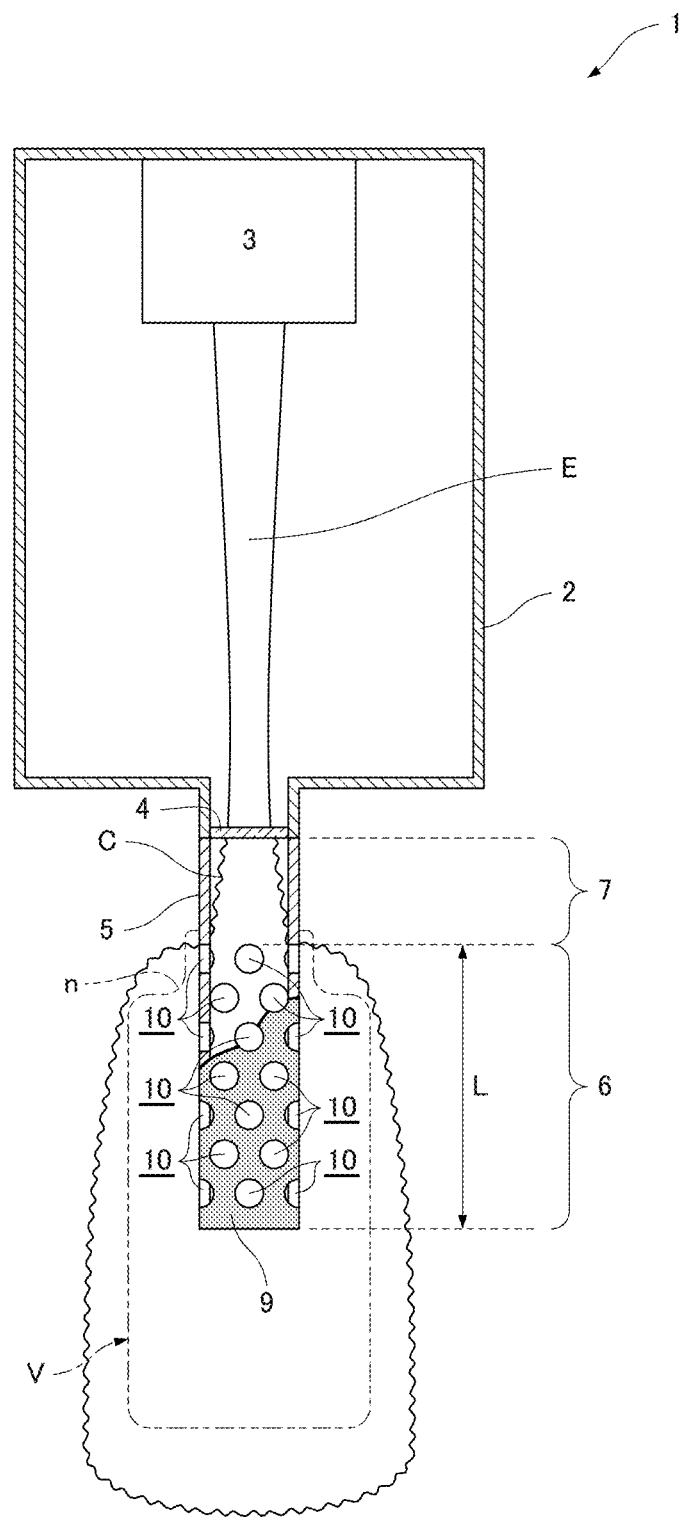
FIG. 1 is a partially cut side view schematically showing an internal surface electron beam-irradiating device according to an embodiment of the present invention.
Figure 13:
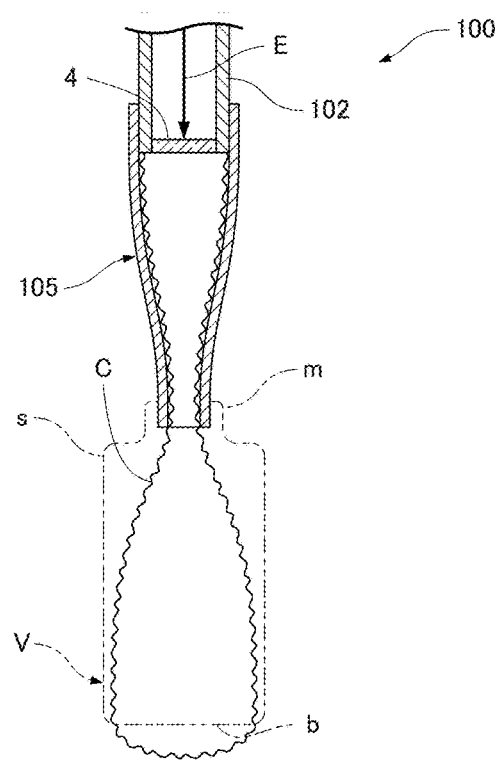
FIG. 13 is a cross-sectional enlarged view showing the vacuum nozzle and an extension nozzle for the internal surface electron beam-irradiating device of the related art.

As shown in FIG. 1, the internal surface electron beam-irradiating device 1 includes, like the internal surface electron beam-irradiating device 100 of the related art shown in FIG. 13, a vacuum chamber 2 with an interior in a vacuum atmosphere, an electron beam generator 3 disposed in the vacuum chamber 2, an output window 4 that is provided on the vacuum chamber 2 and outputs the electron beam E from the electron beam generator 3 to the outside of the vacuum chamber 2, and an extension nozzle 5 that guides an electron cloud C formed by extending the electron beam E emitted from the output window 4. In the following explanation, one end of the extension nozzle 5 near the output window 4 will be referred to as a proximal end, whereas the opposite end will be referred to as a tip. A direction along the proximal end and the tip will be referred to as an axial direction.

The present invention features a leaking section included in the extension nozzle 5. The leaking section 6 leaks the electron cloud C from the tip in a predetermined range L in the axial direction. In the present specification, "leaks the electron cloud C" means that the electron cloud C is partially discharged to the outside while a large volume of the electron cloud C is guided into the leaking section 6. Thus, the leaking section 6 includes empty portions 10 that are formed in a predetermined pattern so as to discharge, to the outside, part of the electron cloud C guided into the leaking section 6. In other words, the leaking section 6 includes the empty portions 10 formed in the predetermined pattern and a component portion 9 other than the empty portions 10, the component portion 9 guiding the electron cloud C into the leaking section 6. Thus, unlike the extension nozzle 5 of the related art shown in FIG. 13, the extension nozzle 5 leaks the electron cloud C through the leaking section 6, in other words, the extension nozzle discharges the electron cloud C with properly reduced directivity. As shown in FIG. 1, the extension nozzle 5 may optionally include a non-leaking section 7 that guides the entire electron cloud C into the leaking section 6 (without discharging the electron cloud C to the outside) near the proximal end (other than the predetermined range L in the extension nozzle 5), although the non-leaking section 7 is not indispensable. The extension nozzle 5 is a combination of the non-leaking section 7 at the proximal side and the leaking section 6 at the tip side. This prevents a neck n of a vial V from being excessively irradiated with the electron beam E and discharges the electron cloud C with a certain degree of directivity, though the degree of directivity is lower than that of the extension nozzle 5 of the related art. The presence or absence of the non-leaking section 7 and the ratio of the range of the non-leaking section 7 to the range of the leaking section are adopted suitably for sterilization according to, for example, the shape of the vial V to be sterilized.

The method of use and the effect of the internal surface electron beam-irradiating device 1 will be discussed below.

First, the tip of the extension nozzle 5 is directed to the opening of the vial V in a state in which the electron beam E is not emitted from the output window 4. Then, the vial V and/or the internal surface electron beam-irradiating device 1 are moved in the axial direction until the leaking section 6 of the extension nozzle 5 is inserted into the opening of the vial V.

Thereafter, multiple electrons are generated from the electron beam generator 3 by, for example, power supplied by a power supply device (not shown). The multiple electrons are accelerated in the vacuum chamber 2 to form the electron beam E emitted to the output window 4. The electron beam E is emitted from the output window 4 into the atmosphere in the extension nozzle 5. The electron beam E emitted from the output window 4 into the extension nozzle 5 collides with air molecules or the like, so that the electron beam E expands into the electron cloud C in the extension nozzle 5. If the extension nozzle 5 includes the non-leaking section 7, the electron cloud C is guided to the leaking section 6 through the non-leaking section 7. If the extension nozzle 5 does not include the non-leaking section 7, the electron cloud C is directly guided to the leaking section 6. In the leaking section 6, the electron cloud C is partially discharged to the outside and thus the directivity of the electron cloud C is properly reduced. Hence, the electron cloud C with the properly reduced directivity from the extension nozzle 5 is suitable for the sterilization of the vial V.

The electron cloud C comes into contact with the internal surface of the vial V, that is, the electron beam E is emitted to the internal surface of the vial V, thereby sterilizing the internal surface of the vial V. When the electron beam E is emitted to the internal surface of the vial V, the vial V and/or the internal surface electron beam-irradiating device 1 may be moved in the axial direction or kept stopped.

After the sterilization of the internal surface of the vial V, the generation of electrons from the electron beam generator 3 is suspended. The vial V and/or the internal surface electron beam-irradiating device 1 are moved in the axial direction until the extension nozzle 5 is completely removed from the opening of the vial V.

When the leaking section 6 of the extension nozzle 5 is inserted into the opening of the vial V, as has been discussed, the emission of the electron beam E is not always stopped. The electron beam E may be continuously emitted.

With this configuration, the internal surface electron beam-irradiating device 1 generates the electron cloud C suitable for sterilizing the vial V (an example of a sterilization object having an opening). Thus, the internal surface of the sterilization object is more uniformly irradiated with the electron beam E, thereby ensuring sufficient sterilization with higher efficiency.

Example 1

The internal surface electron beam-irradiating device 1 according to example 1 more specifically illustrating the embodiment will be described below in accordance with the accompanying drawings.

Figure 2:
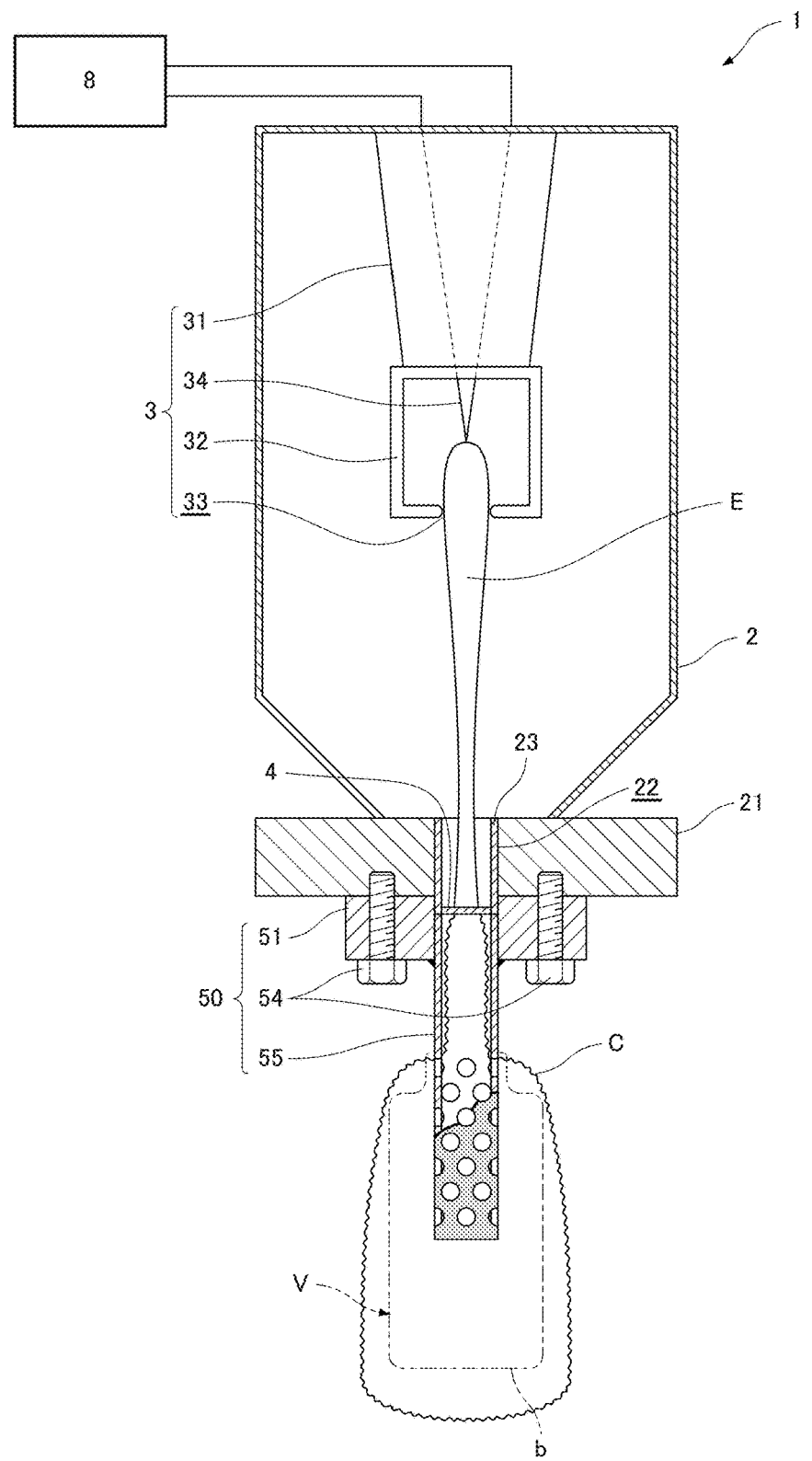
FIG. 2 is a partially cut side view showing the internal surface electron beam-irradiating device according to example 1 of the present, invention.

As shown in FIG. 2, the internal surface electron beam-irradiating device 1 includes the vacuum chamber 2 that acts as a chamber of which interior is evacuated and is optionally provided with a cooling mechanism (not shown), and a mount 21 that seals the vacuum chamber 2. The mount 21 is provided to install the vacuum chamber 2 on other devices or the like. Moreover, the mount 21 has a through hole 22 for passing the electron beam E from the inside of the vacuum chamber 2. The through hole 22 has a cylinder 23 that is disposed along the interior surface of the through hole 22 and protrudes from the mount 21 on the opposite side from the vacuum chamber 2. On the protruding end of the cylinder 23 from the mount 21, the output window 4 made of titanium foil or the like is provided. The vacuum chamber 2 and the mount 21 are tightly connected to each other, the through hole 22 and the cylinder 23 of the mount 21 are tightly connected to each other, and the cylinder 23 and the output window 4 are tightly connected to each other. Thus, a vacuum atmosphere is kept by the vacuum chamber 2, the mount 21, the cylinder 23, and the output window 4 that constitute the internal surface electron beam-irradiating device 1.

The internal surface electron beam-irradiating device 1 includes the electron beam generator 3 that is disposed in the vacuum chamber 2 as a device for generating the electron beam E, and a power supply device 8 that supplies power to the electron beam generator 3. The electron beam generator 3 includes a high voltage terminal 31 that acts as a connecting terminal for power from the power supply device 8, a housing 32 that is connected to the high voltage terminal 31, and a filament 34 that extends from the high voltage terminal 31 into the housing 32 and generates electrons by using the power. The housing 32 has an electron-beam passage hole 33 to guide the electron beam E including electrons generated from the filament 34 in a proper shape to the output window 4.

The internal surface electron beam-irradiating device 1 has an extension nozzle body 50 detachably attached to the protruding side of the cylinder 23 on the mount 21 in order to place the electron cloud C in a state suitable for the sterilization of the vial V. The extension nozzle body 50 includes a connecting plate 51 that can be brought into contact with the mount 21 so as to contain the protruding part of the cylinder 23 and the output window 4, screws 54 that screw the mount 21 and the connecting plate 51, and a nozzle 55 that extends from the connecting plate 51 to the opposite side from the mount 21 so as to guide the electron cloud C from the output window 4.

Figure 3:
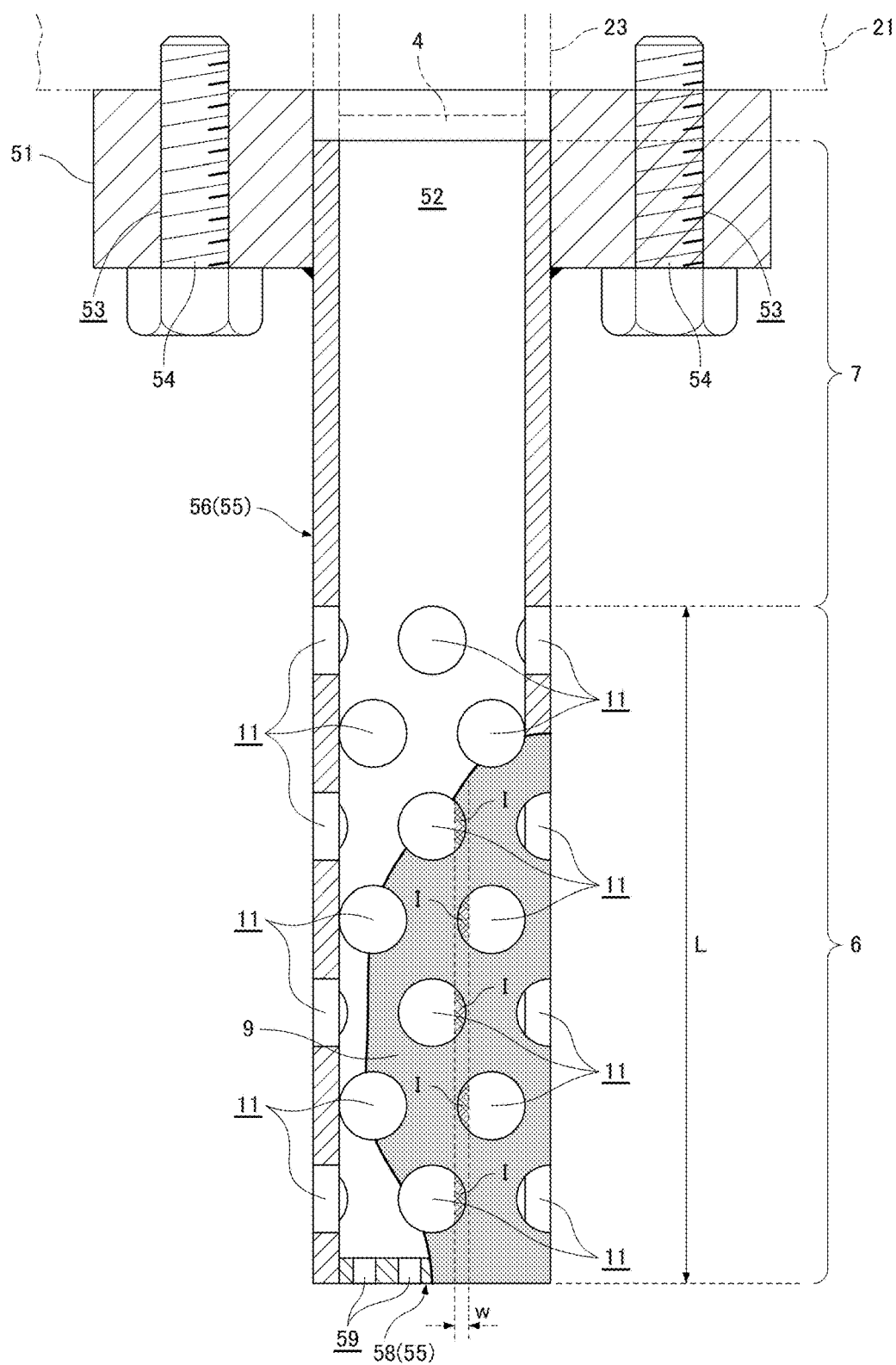
FIG. 3 is a partially cut side view showing an enlarged extension nozzle body for the internal surface electron beam-irradiating device.

Referring to FIG. 3, the configuration of the extension nozzle body 50, a principal part of the present invention, will be specifically described below. In FIG. 3, the electron beam E, the electron cloud C, and the vial V are omitted.

As shown in FIG. 3, the connecting plate 51 has a storage hole 52 at the center of the connecting plate 51, the storage hole 52 passing through the connecting plate 51 and being formed to store the protruding part of the cylinder 23 and the output window 4. The storage hole 52 is formed so as to communicate with the interior of the nozzle 55 and store the cylinder 23 having the same inside diameter as the nozzle 55. Moreover, the connecting plate 51 has a plurality of tapped holes 53 for screwing the screws 54 from the nozzle 55 side to the mount 21 side, the tapped holes 53 being formed at regular intervals on a circle centered around the storage hole 52 (For example, the two tapped holes 53 are shown in FIGS. 1 to 3).

As shown in FIG. 3, the screws 54 are long enough to screw the connecting plate 51 to the mount 21. The mount 21 is tapped at portions to be screwed onto the screws 54.

The nozzle 55 has a long cylindrical part 56 joined to the connecting plate 51 at a position where the interior of the nozzle 55 communicates with the storage hole 52, and a lid part 58 disposed over the tip of the long cylindrical part 56. On the long cylindrical part 56, multiple round holes 11 are formed in a predetermined pattern over a predetermined range L from the tip in the axial direction. The round holes 11 are formed for discharging, to the outside, part of the electron cloud C guided into the long cylindrical part 56. In the long cylindrical part 56, the leaking section 6 is equivalent to the predetermined range L from the tip in the axial direction, that is, the range where the multiple round holes 11 are formed in the predetermined pattern. The round holes 11 are equivalent to the empty portions 10 of the foregoing embodiment. A part other than the round holes 11 (empty portions 10) in the leaking section 6 is equivalent to the component portion 9. The round holes 11 having perfect circular shapes in FIGS. 2 and 3 may be oval-like in shape.

To be more precise, the leaking section 6 ranges from the tip of the nozzle 55 to the proximal sides of the round holes 11 at the most proximal side of the nozzle 55. The non-leaking section 7 is a range including a part other than the leaking section 6 on the long cylindrical part 56 and the tip side from the output window 4 in the storage hole 52 formed at a connecting plate 51.

The multiple round holes 11 are formed in the predetermined pattern on the long cylindrical part 56 of the nozzle 55 as follows: the multiple round holes 11 are circumferentially formed at regular intervals and are axially formed at regular intervals on the long cylindrical part 56. The leaking section 6 always includes the round holes 11 at each width w in the circumferential direction and over the range in the axial direction. Parts of the round holes included by the width w are shown by the reference numeral I. This is because even if the component portion 9 blocks the discharge of the electron cloud C at a predetermined point, in other words, even if the component portion 9 causes insufficient irradiation with the electron beam E at the predetermined point, the irradiation with the electron beam E at the predetermined point is compensated for by axially moving the nozzle 55 (specifically, the leaking section 6) inserted into the opening of the vial V, and/or the vial V. Thus, the internal surface of the vial V is quite uniformly irradiated with the electron beam E.

The multiple round holes 11 in FIGS. 2 and 3 are all identical in size but may be increased in size toward the proximal side. The multiple round holes 11 in FIGS. 2 and 3 are disposed at regular intervals but the intervals may be reduced toward the proximal side. The round holes 11 increased in size at the decreasing intervals cause the degree of discharge of the electron cloud C through the round holes 11 to increase toward the proximal side. Thus, the electron cloud C prone to be discharged to a higher degree from the tip side is sufficiently discharged also from the proximal side. Thus, the vial V is more properly sterilized.

In the leaking section 6, the total area of the round holes 11 (empty portions 10) may be larger than the total area of the part other than the round holes 11 (component portion 9). With this configuration, the electron cloud C is sufficiently discharged to the outside of the long cylindrical part 56, thereby more properly sterilizing the vial V.

In this way, in addition to the effect of the foregoing embodiment, the internal surface electron beam-irradiating device 1 of example 1 can quite uniformly irradiate the internal surface of a sterilization object with the electron beam E. This ensures sufficient sterilization with higher efficiency.

Example 2

Figure 4:
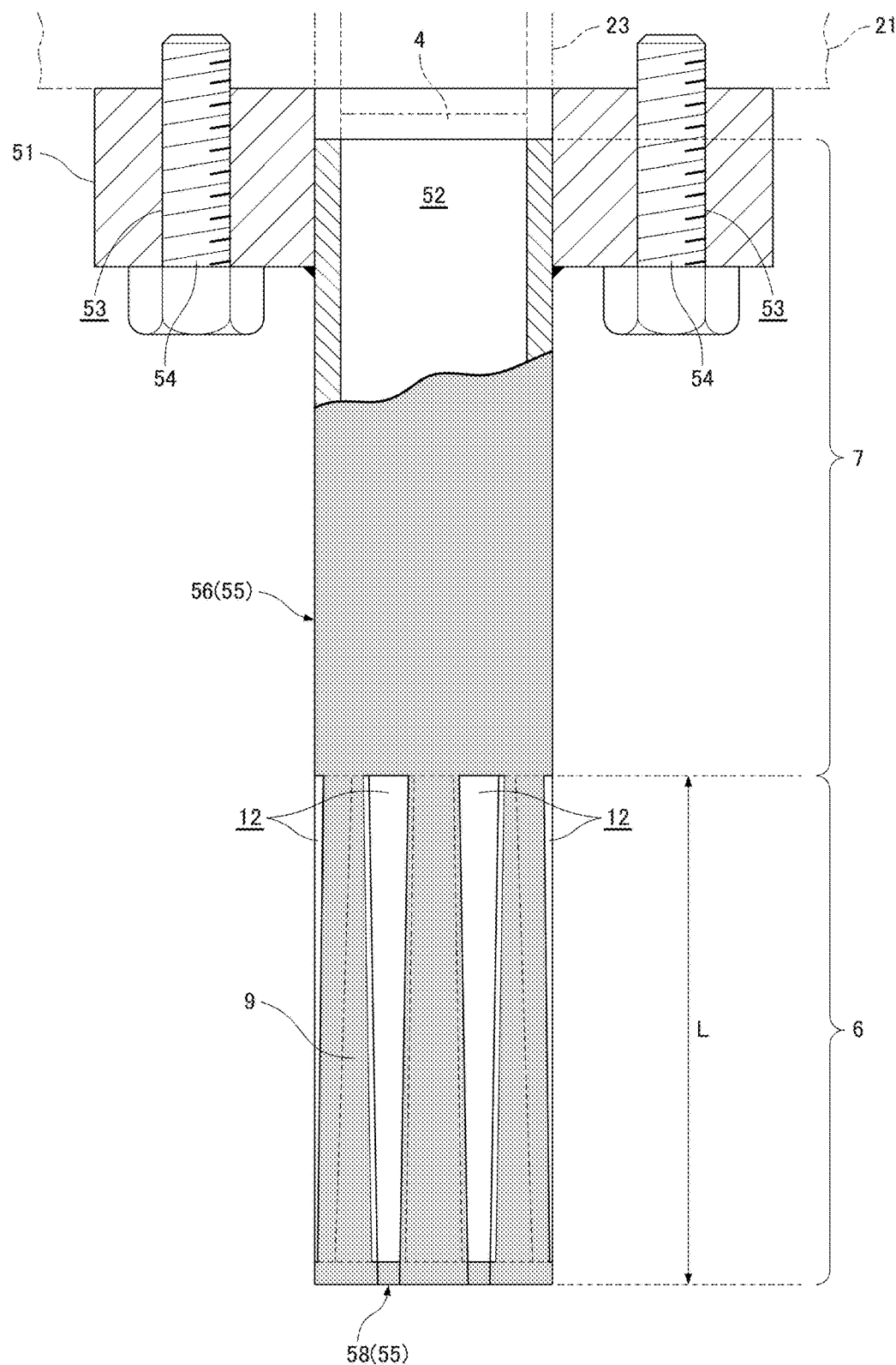
FIG. 4 is a partially cut side view showing an enlarged extension nozzle body for the internal surface electron beam-irradiating device according to example 2 of the present invention.

The internal surface electron beam-irradiating devices 1 of example 1 and example 2 are different from each other only in the leaking section 6. In the leaking section 6 of example 1, the multiple round holes 11 are formed in the predetermined pattern on the long cylindrical part 56, whereas in the leaking section 6 of example 2, a plurality of slits 12 are axially formed in a predetermined pattern on the long cylindrical part 56 as shown in FIG. 4. Thus, the slits 12 are equivalent to the empty portions 10 of the foregoing embodiment and a part other than the slits 12 (empty portions 10) in the leaking section 6 is equivalent to the component portion 9.

Referring to FIG. 4, the internal surface electron beam-irradiating device 1 of example 2 will be described below. The leaking section 6 different from that of example 1 will be mainly discussed. The same configurations as those of example 1 are indicated by the same reference numerals and the explanation thereof is omitted.

The multiple slits 12 are formed in a predetermined pattern on the long cylindrical part 56 of the nozzle 55 as follows. The multiple slits 12 are formed on the long cylindrical part 56 so as to be each cut from the tip and are disposed at regular intervals in the circumferential direction. Moreover, the widths of the slits 12 in the circumferential direction increase toward the proximal side. Specifically, in the leaking section 6, the areas of the empty portions 10 (slits 12) increase toward the output window 4. With this configuration, the electron cloud C prone to be discharged to a higher degree from the tip side is sufficiently discharged also from the proximal side. The configuration of FIG. 4 is an example where the area ratio of the empty portions 10 (slits 12) and the component portion 9 in the circumferential direction of the leaking section 6 is different in the axial direction (a direction orthogonal to the circumferential direction).

In this way, in addition to the effect of the foregoing embodiment, the internal surface electron beam-irradiating device 1 according to example 2 sufficiently discharges the electron cloud C from the proximal side, thereby more properly sterilizing the vial V. This ensures sufficient sterilization with higher efficiency.

Example 3

The internal surface electron beam-irradiating device 1 of example 3 is different from those of example 1 and example 2 only in the leaking section 6. In the leaking section 6 of example 1 or example 2, the multiple round holes 11 or the multiple axial slits 12 are formed in the predetermined pattern on the long cylindrical part 56, whereas in the leaking section 6 of example 3, the long cylindrical part 56 includes a mesh 57 as shown in FIG. 5.

Figure 5:
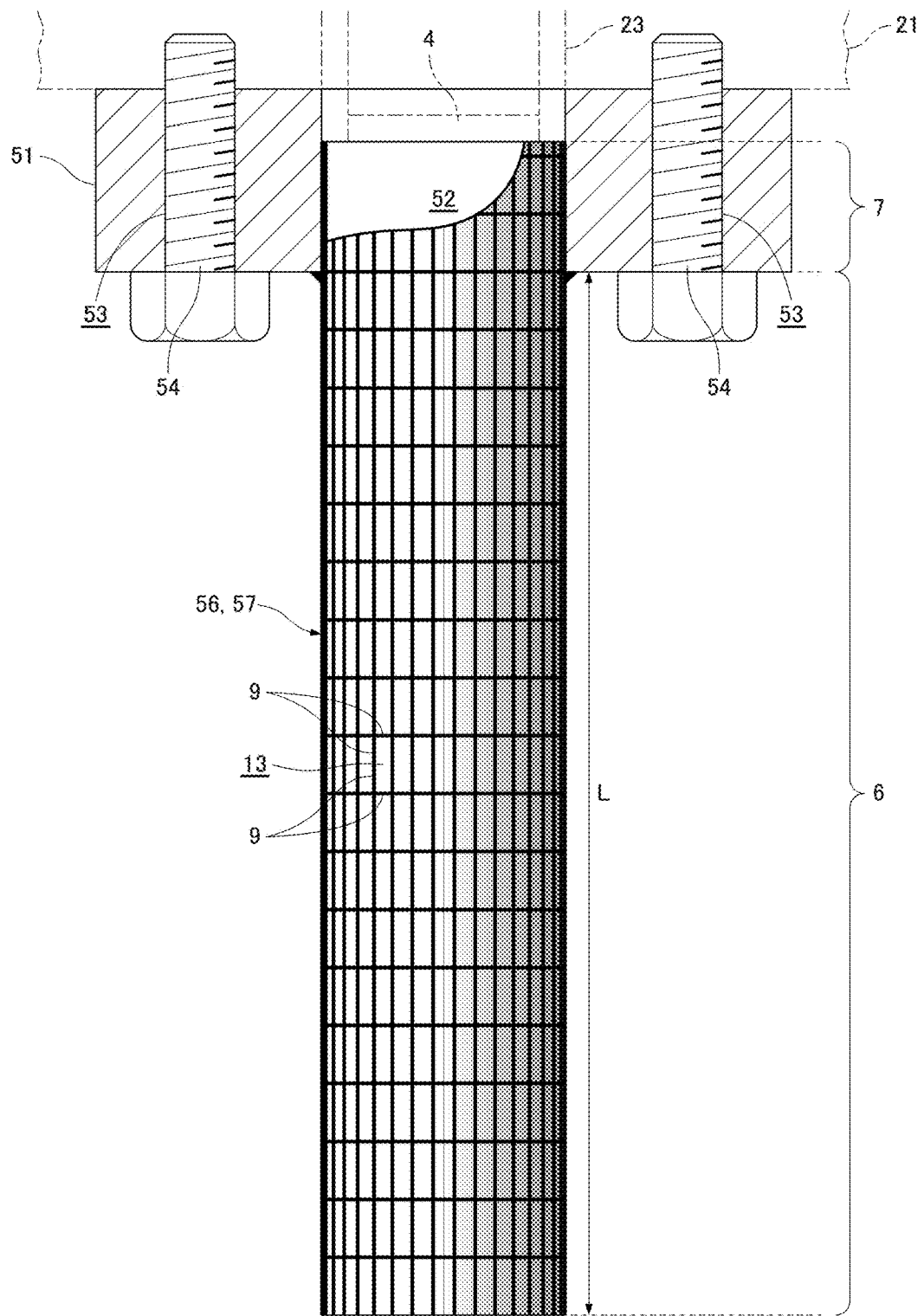
FIG. 5 is a partially cut side view showing an enlarged extension nozzle body for the internal surface electron beam-irradiating device according to example 3 of the present invention.

Referring to FIG. 5, the internal surface electron beam-irradiating device 1 of example 3 will be described below. The leaking section 6 different from those of example 1 and example 2 will be mainly discussed. The same configurations as those of example 1 and example 2 are indicated by the same reference numerals and the explanation thereof is omitted.

The mesh 57 constituting the leaking section 6 is formed by knitting wires 9 into a net and thus includes squares 13 disposed between the wires 9 and the wires 9 extending in the axial and circumferential directions. Thus, the squares 13 are equivalent to the empty portions 10 of the foregoing embodiment and the wires 9 are equivalent to the component portion 9.

In the leaking section 6, the total area of the squares 13 (empty portions 10) is larger than the total area of the wires 9 (component portion 9). With this configuration, the electron cloud C is sufficiently discharged to the outside of the long cylindrical part 56, thereby properly sterilizing the vial V.

In this way, in addition to the effect of the foregoing embodiment, the internal surface electron beam-irradiating device 1 of example 3 sufficiently discharges the electron cloud C to the outside of the long cylindrical part 56, thereby more properly sterilizing the vial V. This ensures sufficient sterilization with higher efficiency.

Examples 4 to 6

Figure 6:
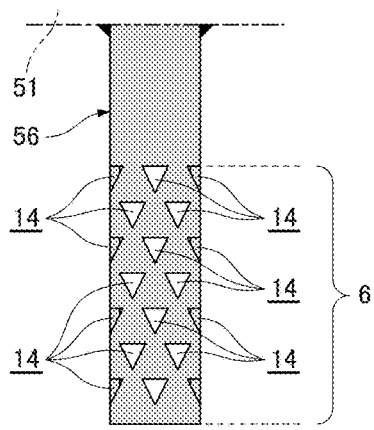
FIG. 6 is a side view showing an enlarged nozzle in the extension nozzle body for the internal surface electron beam-irradiating device according to example 4 of the present invention.
Figure 7:
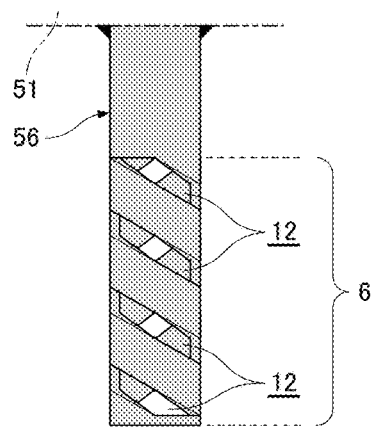
FIG. 7 is a side view showing an enlarged nozzle in the extension nozzle body for the internal surface electron beam-irradiating device according to example 5 of the present invention.
Figure 8:
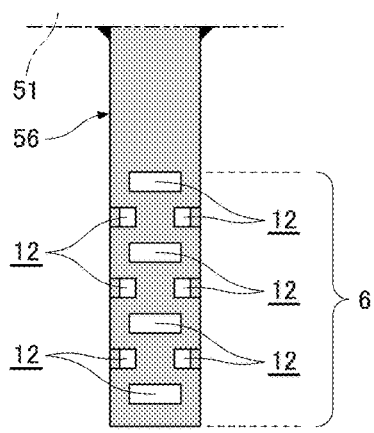
FIG. 8 is a side view showing an enlarged nozzle in the extension nozzle body for the internal surface electron beam-irradiating device according to example 6 of the present invention.

In addition to examples 1 to 3 described as main examples, examples 4 to 6 are shown in FIGS. 6 to 8. Examples 4 to 6 are different from examples 1 to 3 only in the leaking section 6.

In the leaking section 6 of example 4 shown in FIG. 6, the round holes 11 of example 1 are replaced with triangle holes 14. In the leaking section 6 of example 5 shown in FIG. 7, the axial slits 12 of example 2 are inclined in the circumferential direction. In the leaking section 6 of example 3 shown in FIG. 8, the axial slits 12 of example 2 are extended in the circumferential direction instead of the axial direction. One of examples 4 to 6 is optionally adopted according to the shape of the vial V.

As has been discussed, the extension nozzle bodies 50 according to examples 1 to 6 are detachably attached to the mount 21 with the screws 54. Thus, one of the extension nozzle bodies 50 is optionally attached to the mount 21 according to the shape of the vial V.

The lid part 58 was not specifically discussed in the foregoing embodiment and examples 1 to 5. The lid part 58 may completely cover the tip of the long cylindrical part 56. The lid part 58 may be formed holes 59 or the provided mesh 57 for leaking the electron cloud C. For the holes 59 of the lid part 58 shown in FIG. 3, a proper size and pattern are adopted according to desired irradiation of a bottom b of the vial V with the electron beam E. If the bottom b of the vial V needs to be sufficiently irradiated with the electron beam E, the lid part 58 may not be provided.

Figure 9:
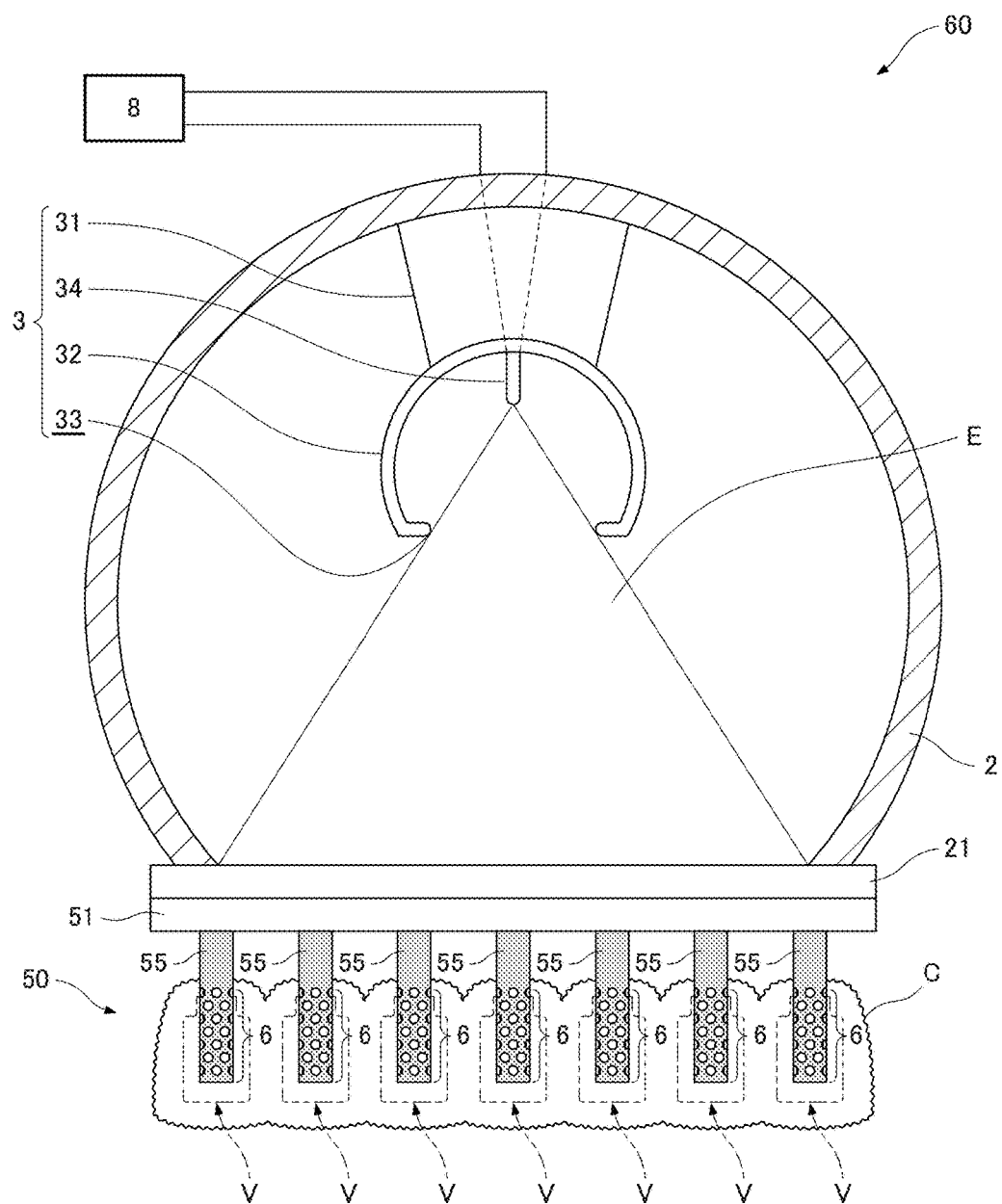
FIG. 9 is a partially cut side view showing an internal surface electron beam-irradiating device according to another embodiment of the present invention.

In the foregoing embodiment and examples 1 to 6, the internal surface electron beam-irradiating device 1 sterilizes the internal surface of the single vial V. As shown in FIG. 9, the internal surfaces of multiple vials V may be simultaneously sterilized by an internal surface electron beam-irradiating device 60. Unlike in examples 1 to 6, the internal surface electron beam-irradiating device 60 includes, not one, multiple through holes 22 (not shown) formed on a mount 21, multiple cylinders 23 (not shown) disposed along the internal surfaces of the through holes 22, multiple output windows 4 (not shown) provided on the cylinders 23, and multiple storage holes 52 (not shown) and nozzles 55 of an extension nozzle body 50. An electron beam generator 3 is configured such that an electron beam E in a vacuum chamber 2 reaches all the nozzles 55. A leaking section 6 is adopted according to any one of examples 1 to 6. The configuration of FIG. 9 simultaneously sterilizes the internal surfaces of the multiple vials V in addition to the effects of examples 1 to 6, thereby remarkably improving the efficiency of sterilization.

Moreover, in the foregoing embodiment and examples 1 to 6, the shapes of the extension nozzle 5 and the nozzle 55 in cross section were not described. The shapes are not particularly limited and thus any one of circular and angular shapes may be used. A preferable shape is adopted according the shape of the vial V in cross section.

Furthermore, in the foregoing embodiment and examples 1 to 6, the extension nozzle 5 and the nozzle 55 are identical in width in the axial direction. The nozzles may be increased or reduced in width toward the tip side according to desired irradiation of the bottom b of the vial V with the electron beam E.

In examples 1 to 6, the extension nozzle body 50 is detachably attached to the mount 21 with the screws 54. The extension nozzle body 50 may be detachably attached with fasteners other than the screws 54 or the extension nozzle body 50 may not be detachable.

Figure 10:
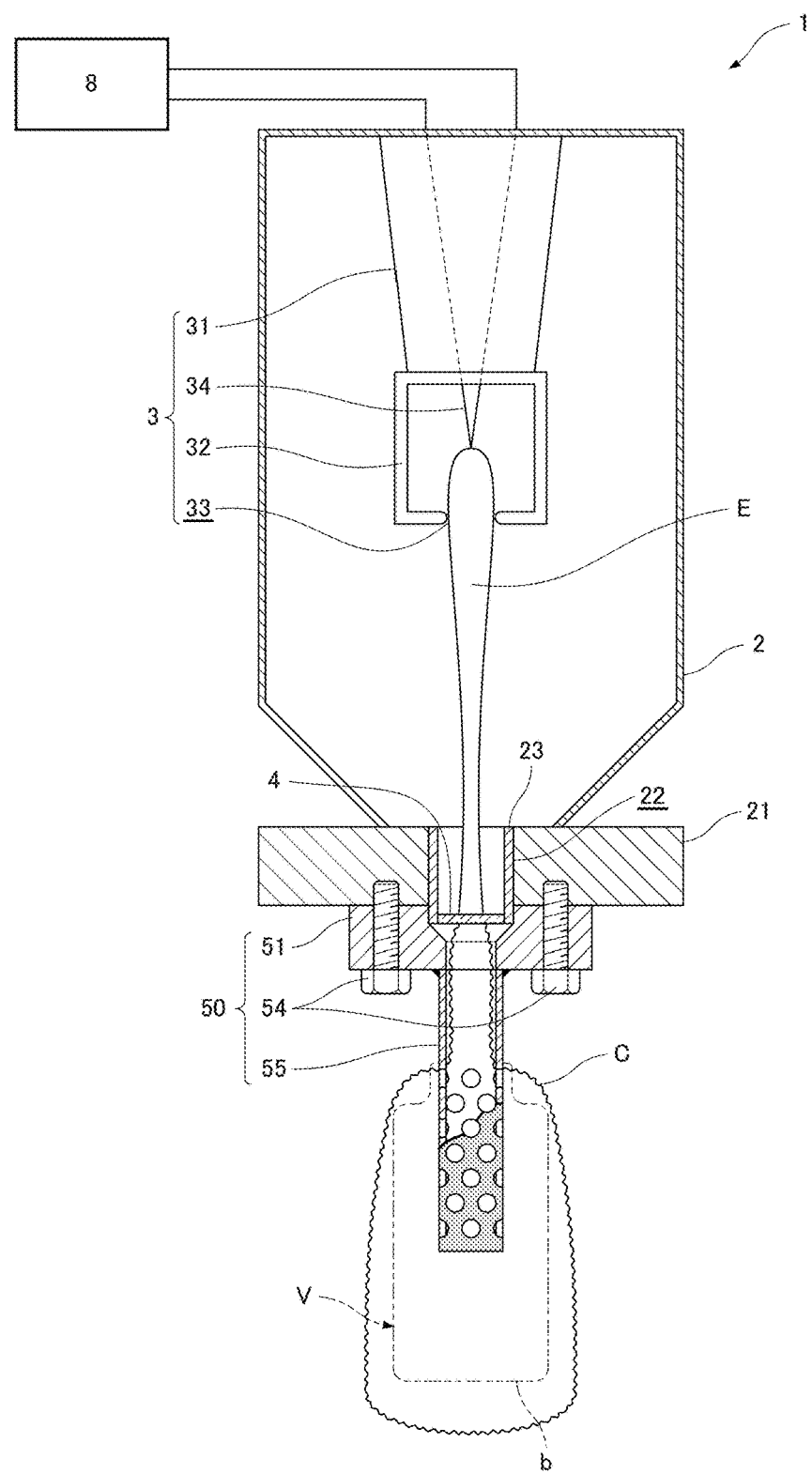
FIG. 10 is a partially cut side view showing an internal surface electron beam-irradiating device according to still another embodiment of the present invention.
Figure 11:
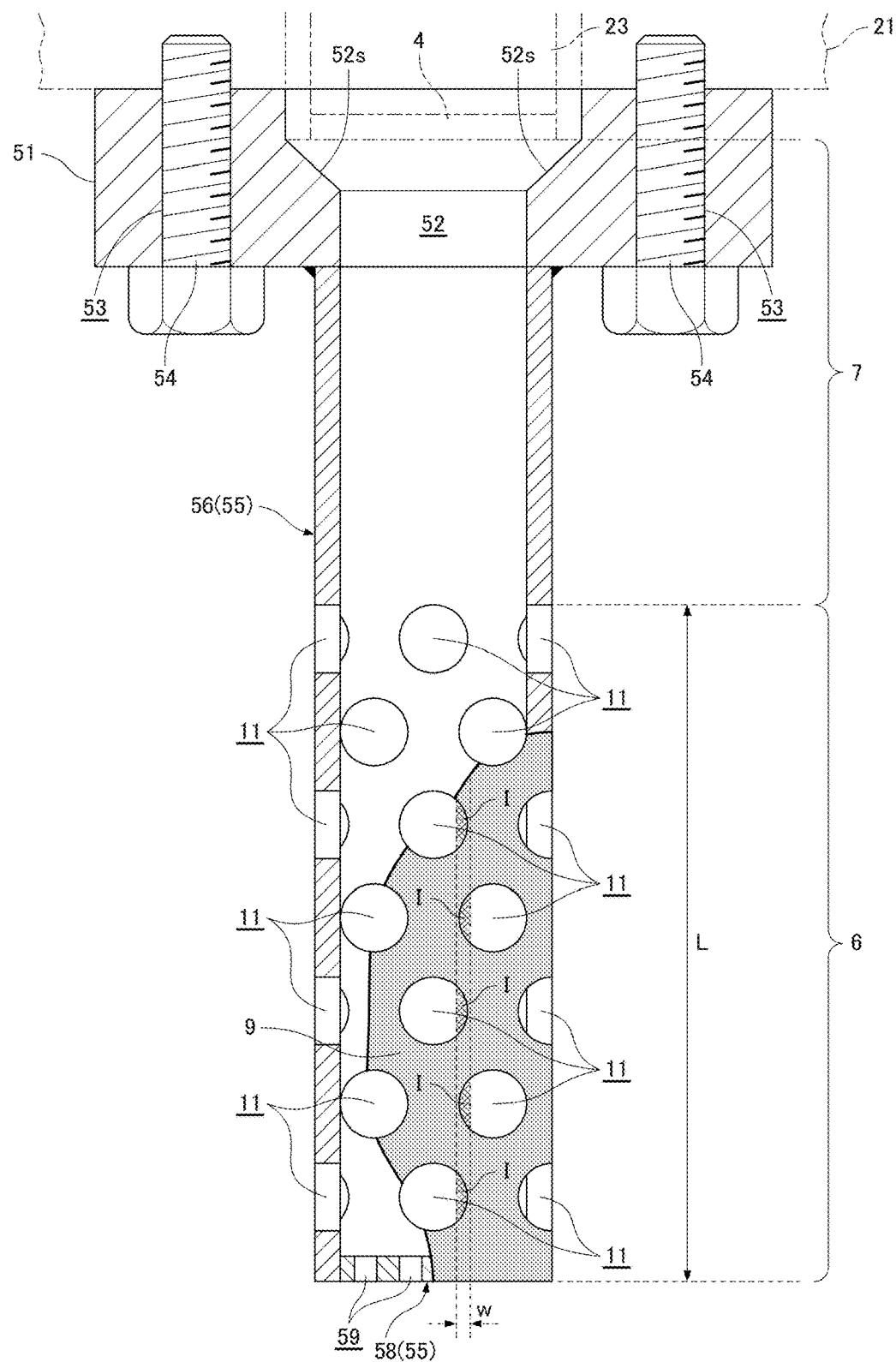
FIG. 11 is a partially cut side view showing an enlarged extension nozzle body for the internal surface electron beam-irradiating device.
Figure 12:
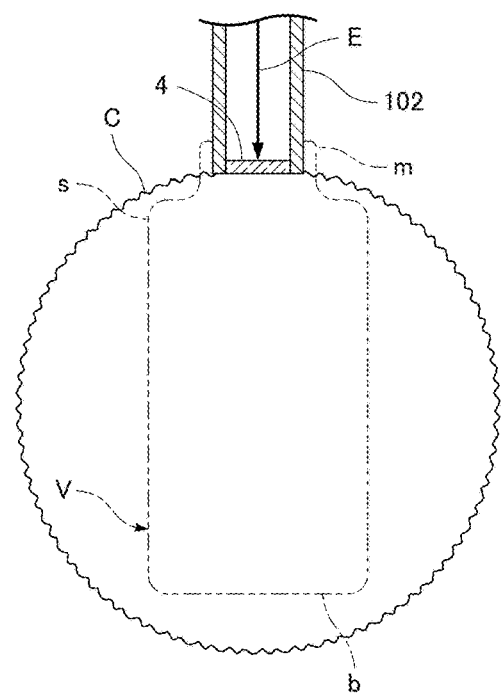
FIG. 12 is a cross-sectional enlarged view showing a vacuum nozzle for a widely known internal surface electron beam-irradiating device of the related art.

In examples 1 to 6, the storage hole 52 has a constant inside diameter in the axial direction. The inside diameter of the storage hole 52 is however not limited to the constant inside diameter. For example, as shown in FIGS. 10 and 11, the storage hole 52 has a decreasing diameter 52s from the mount 21 to the nozzle 55 to stabilize the protruding part of the stored cylinder 23 and the output window 4. However, the decreasing diameter 52s is preferably set without interfering with the electron cloud C from the output window 4.

In examples 1 to 6, the cylinder 23 disposed in the through hole 22 was discussed. The output window 4 may be provided in direct contact with the through hole 22 in the absence of the cylinder 23.

In examples 1 to 6, configurations other than that described in the foregoing embodiment are optional and thus can be omitted and changed as necessary.

The invention claimed is:

1. An internal surface electron beam-irradiating device for sterilizing an internal surface of a sterilization object having an opening by irradiation with an electron beam,
the device comprising:
an electron beam generator configured to generate the electron beam;
a vacuum chamber containing the electron beam generator;
an output window configured to emit the electron beam to outside of the vacuum chamber; and
an extension nozzle configured to guide an electron cloud formed by extending the electron beam emitted from the output window,
the extension nozzle including a leaking section configured to leak the electron cloud,
the leaking section including empty portions configured to discharge part of the electron cloud to the outside, and a component portion configured to guide the electron cloud into the leaking section.

2. The internal surface electron beam-irradiating device according to claim 1, wherein the leaking section includes the empty portions at each width in a circumferential direction over a range from an end of the leaking section near the output window to an opposite end of the leaking section.

3. The internal surface electron beam-irradiating device according to claim 1, wherein an area ratio of the empty portions and the component portion in the circumferential direction of the leaking section is different from an area ratio in a direction orthogonal to the circumferential direction.

4. The internal surface electron beam-irradiating device according to claim 1, wherein the leaking section is configured such that a total area of the empty portions is larger than a total area of the component portion.

* * * * *